(12) United States Patent
Karni

(10) Patent No.: US 10,765,883 B2
(45) Date of Patent: Sep. 8, 2020

(54) VAGINAL TIGHTENING AND TREATMENT OF WRINKLES

(71) Applicant: Zlasers Ltd., Kfar Shemaryahu (IL)

(72) Inventor: Ziv Karni, Kfar Shemaryahu (IL)

( * ) Notice: Subject to any disclaimer, the term of this patent is extended or adjusted under 35 U.S.C. 154(b) by 119 days.

(21) Appl. No.: 16/018,186

(22) Filed: Jun. 26, 2018

(65) Prior Publication Data

US 2019/0388703 A1    Dec. 26, 2019

(51) Int. Cl.
*A61N 5/06* (2006.01)
*A61B 18/14* (2006.01)
*A61B 18/00* (2006.01)
*A61N 5/067* (2006.01)

(52) U.S. Cl.
CPC ........ *A61N 5/0603* (2013.01); *A61B 18/1492* (2013.01); *A61B 2018/00559* (2013.01); *A61B 2018/00577* (2013.01); *A61N 2005/063* (2013.01); *A61N 2005/067* (2013.01); *A61N 2005/0611* (2013.01); *A61N 2005/0658* (2013.01)

(58) Field of Classification Search
None
See application file for complete search history.

(56) References Cited

U.S. PATENT DOCUMENTS

| 7,238,179 | B2* | 7/2007 | Brucker ................. A61B 18/22 606/15 |
| 10,080,908 | B2* | 9/2018 | Kazic .................. A61N 5/0603 |
| 2011/0301584 | A1 | 12/2011 | Beck |
| 2016/0120699 | A1* | 5/2016 | Farley ................. A61F 9/00736 606/4 |

FOREIGN PATENT DOCUMENTS

| EP | 2957322 | 12/2015 |
| WO | 2012/092508 | 7/2012 |

OTHER PUBLICATIONS

PCT Search Report and Written Opinion PCT/IB2019/055283, dated Nov. 6, 2019.

* cited by examiner

*Primary Examiner* — Brian T Gedeon
(74) *Attorney, Agent, or Firm* — Dekel Patent Ltd; David Klein

(57) ABSTRACT

A system includes a laser source coupled to an optical waveguide which has a laser output portion, and a vaginal housing transparent to laser energy which is emitted by the laser source and which exits the laser output portion, wherein the optical waveguide is movable along a path inside the vaginal housing.

8 Claims, 1 Drawing Sheet

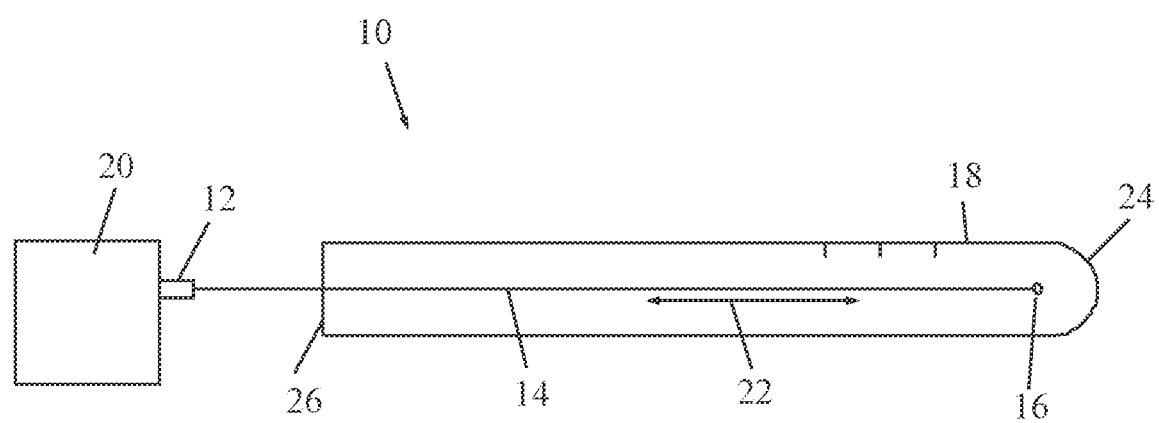

VAGINAL TIGHTENING AND TREATMENT OF WRINKLES

FIELD OF THE INVENTION

The present invention generally relates to vaginal rejuvenation, and more particularly to a laser-based system and method for vaginal rejuvenation.

BACKGROUND OF THE INVENTION

Vaginal relaxation is the loss of the optimum structural architecture of the vagina. This process is generally associated with natural aging and childbirth, whether vaginal or not. Multiple pregnancies increase the alteration of these structures. During the vaginal relaxation process, the vaginal muscles become relaxed with poor tone, strength, control and support. The internal and external vaginal diameters can greatly increase with significant stretching of vaginal walls.

Recently new modalities for treatment of aged vaginal walls have been introduced, based on skin resurfacing and skin tightening methods, both ablative and non-ablative. The goal of vaginal rejuvenation is to induce tightening and promote new collagen regeneration.

In ablative procedures, the upper layer of the skin is either fully removed (bulk removal) or partially removed (fractional treatment).

Lasers commonly used for ablative removal are $CO_2$ laser (wavelength of 10.6 µm) or Er:YAG laser (erbium-doped yttrium aluminum garnet) (wavelength of 2.94 µm), both of which have strong water absorption. Other lasers have been proposed, such as Tm:YAG (wavelength of 2.0 µm), Ho:YAG (wavelength of 2.1 µm), and Er,Cr:YSGG (erbium, chromium-doped yttrium scandium gallium garnet) (wavelength of 2.78 or 2.79 µm).

Different methods have been proposed for non-ablative procedures. For example, ablative lasers (like $CO_2$ or Er:YAG) are used in a long pulse mode below the ablation threshold, so as to cause thermal effects due to conduction of the heat to the tissue but without ablation of the tissue. Other lasers have been used with a non-ablative wavelength with low water or blood absorption so that the effect is purely thermal and non-ablative.

Laser energy is applied to the vaginal walls through an opening in a tube which is inserted in the vagina. The tube is rotated so that the laser energy exits the opening at intervals of 90° or other angular interval; the tube is then moved proximally back (about 1 cm) and the procedure is repeated until the length of the vagina is covered. The procedure can be done multiple times in the same session.

In all laser technologies, in order to be effective, the laser beam must be focused on the vagina wall. However, focusing is often impossible since the vaginal wall is not straight or smooth; rather it contains many wrinkles.

Other methods include heating by means of ultrasonic energy or RF energy (bipolar or monopolar) at different RF frequencies, between 0.5-40 MHz. However, in RF treatment, the RF electrodes must be in tight contact with the vagina wall so that RF impedance closely matches the tissue so that the RF energy is not reflected back. This is difficult to achieve and may cause discomfort to the patient. The procedure time is disadvantageously long in order to be effective.

SUMMARY OF THE INVENTION

The present invention seeks to provide a novel and improved laser-based system and method for vaginal rejuvenation, as described in detail below. The system and method do not have the abovementioned disadvantages of the prior art.

There is thus provided in accordance with a non-limiting embodiment of the present invention a system including a laser source coupled to an optical waveguide (e.g., fiber optic) which has a laser output portion, and a vaginal housing transparent to laser energy which is emitted by the laser source and which exits the laser output portion, wherein the optical waveguide (e.g., fiber optic) is movable along a path inside the vaginal housing.

In accordance with a non-limiting embodiment of the present invention the path is a longitudinal linear path.

In accordance with a non-limiting embodiment of the present invention the path is a rotational path.

In accordance with a non-limiting embodiment of the present invention the laser source is a diode laser and the optical waveguide is an optical fiber.

In accordance with a non-limiting embodiment of the present invention the vaginal housing includes a tubular structure with a distal end, which may be rounded and closed.

In accordance with a non-limiting embodiment of the present invention the optical waveguide is coupled to an actuator configured to move the optical waveguide along the path.

In accordance with a non-limiting embodiment of the present invention the optical fiber includes a side-firing fiber, or a radial fiber or a diffused end portion fiber.

In accordance with a non-limiting embodiment of the present invention a method of using the system includes inserting the vaginal housing into a vagina and applying laser energy to a vaginal wall by application of laser energy from the laser output portion and moving the optical waveguide along the path and repeating application of laser energy from the laser output portion without moving the vaginal housing, wherein the application of laser energy causes non-ablative remodeling of collagen in the vaginal wall.

In accordance with a non-limiting embodiment of the present invention the vaginal housing does not touch the vaginal wall.

In accordance with a non-limiting embodiment of the present invention the laser energy is not focused.

BRIEF DESCRIPTION OF THE DRAWINGS

The present invention will be understood and appreciated more fully from the following detailed description, taken in conjunction with the drawings in which:

FIG. 1 is a simplified illustration of a laser-based system and method for vaginal rejuvenation, in accordance with a non-limiting embodiment of the present invention.

DETAILED DESCRIPTION OF EMBODIMENTS

Reference is now made to FIG. 1, which illustrates a laser-based vaginal rejuvenation system 10, constructed and operative in accordance with a non-limiting embodiment of the present invention.

The system 10 includes a laser source 12 coupled to an optical waveguide 14 which has a laser output portion 16. The laser source 12, optical waveguide 14 and laser output portion 16 are also collectively referred to as the laser. The optical waveguide 14 is movable inside a vaginal housing 18, which is transparent to the laser energy emitted by the laser source 12 and which exits the laser output portion 16.

The optical waveguide 14 is coupled to an actuator 20 configured to move optical waveguide 14 along a longitudinal path 22 inside vaginal housing 18.

The vaginal housing 18 may be a tubular structure with a distal end 24, which may be rounded and closed. In another option, distal end 24 is open or openable, which may be advantageous for enabling the laser output portion 16 to distally protrude out of the housing for external laser treatment of the genital labia. Of course, this external treatment may also be done with the laser output portion 16 inside the housing with a closed distal end. The vaginal housing 18 may be constructed of glass, plastic or any other suitable material transparent to the laser energy emitted by the laser. Without limitation, vaginal housing 18 may be a transparent tube with an OD of 3-20 mm and ID of 1-18 mm, or preferably OD of 9-10 mm and ID 1-3 mm. The proximal end 26 of vaginal housing 18 may be sealed. The vaginal housing 18 may include depth markings and/or longitudinal marking for side fiber option.

Actuator 20 may be, without limitation, a servomotor, linear actuator, or a simple displacement mechanism using an off-center arm on a rotating wheel to displace the fiber in and out at a controlled rotational speed.

Instead of using actuator 20, the displacement of the fiber inside the tube can be done manually.

In a preferred embodiment, laser source 12 is a diode laser and optical waveguide 14 is an optical fiber (that is, the laser is a diode fiber laser).

The non-ablative treatment may be carried out with different laser wavelengths that have different absorption coefficients so that the laser energy penetration can be at different tissue depths.

The wavelengths can be individual wavelengths or a combination of wavelengths, such as but not limited to: 980 nm (medium depth of penetration), 1064 nm (greater depth of penetration) or 1470 nm (more superficial depth of penetration). All of these wavelengths can be achieved with a diode laser with a power of 5-60 watts (continuous or pulsed).

Without limitation, the laser energy can be transmitted in a fiber optics with a diameter of 300-1000 µm.

The optical fibers may be, without limitation: a side-firing fiber which can emit the energy at angles such as 70-90° from the optical axis; a radial fiber, which emits light at 360° from the optical axis; or a diffused end portion fiber, in which light is scattered around the distal end, so that the light-emitting pattern of the diffusing fiber exhibits a uniform distribution along the distal end (e.g., the diffused distal part may be 0.5-4 cm in length and emits the light at 360° along the diffused length).

In use, the vaginal housing 18 is easily inserted into the vagina due its small diameter. The vaginal housing 18 does not need to touch the vaginal wall since the laser beam is not focused; thus there is no need for contact with the vaginal wall.

Different modes of treatment may be used depending on the laser used. For example, for a side-fire fiber, the fiber may be rotated 360° by actuator 20 around the axis 22 in order to cover the entire inner circumference of the vaginal wall. The fiber is then displaced incrementally linearly and proximally along axis 22 (e.g., about 1 cm) and the laser procedure is repeated.

For a 360° radial fiber or diffused fiber laser (higher laser power), there is no need to rotate the fiber and the fiber is only displaced linearly and incrementally. The incremental steps may be larger for a diffused laser (e.g., between 1-40 mm).

By maintaining the vaginal housing 18 in a stationary position in the vagina and moving the fiber inside the tube, there is no discomfort to the patient, which is a significant advantage over the prior art. In this manner, the collagen along the vagina length is thermally treated effectively, painlessly and rapidly.

What is claimed is:

1. A system comprising:
a laser source coupled to an optical waveguide which has a laser output portion; and
a vaginal housing transparent to laser energy which is emitted by said laser source and which exits said laser output portion, wherein said optical waveguide is movable along a path inside said vaginal housing, wherein said vaginal housing is a tubular structure with an openable distal end, and wherein said laser output portion has a first operable position inside said vaginal housing and a second operable position in which said distal end is open and said laser output portion protrudes out of said vaginal housing through said distal end.

2. The system according to claim 1, wherein said path is a longitudinal linear path.

3. The system according to claim 1, wherein said path is a rotational path.

4. The system according to claim 1, wherein said laser source is a diode laser and said optical waveguide is an optical fiber.

5. The system according to claim 1, wherein said optical waveguide is coupled to an actuator configured to move said optical waveguide along said path.

6. A method comprising using the system of claim 1, inserting said vaginal housing into a vagina and applying laser energy to a vaginal wall by application of laser energy from said laser output portion and moving said optical waveguide along the path and repeating application of laser energy from said laser output portion without moving said vaginal housing, wherein the application of laser energy causes non-ablative remodeling of collagen in the vaginal wall.

7. The method according to claim 6, wherein said vaginal housing does not touch the vaginal wall.

8. The method according to claim 6, comprising opening said distal end and causing said laser output portion to distally protrude out of said vaginal housing through said distal end and to apply laser energy with said laser output portion for external laser treatment of genital labia.

* * * * *